United States Patent
Kelly

(10) Patent No.: US 11,351,307 B2
(45) Date of Patent: Jun. 7, 2022

(54) ADJUSTABLE DOSE DRUG DELIVERY SYSTEM

(71) Applicant: Beloteca, Inc., San Diego, CA (US)

(72) Inventor: Lawrence J. Kelly, Fairfield, OH (US)

(73) Assignee: Beloteca Investment Fund 1, LLC, San Diego, CA (US)

( * ) Notice: Subject to any disclaimer, the term of this patent is extended or adjusted under 35 U.S.C. 154(b) by 595 days.

(21) Appl. No.: 16/346,849

(22) PCT Filed: Nov. 6, 2017

(86) PCT No.: PCT/US2017/060128
§ 371 (c)(1),
(2) Date: May 1, 2019

(87) PCT Pub. No.: WO2018/085759
PCT Pub. Date: May 11, 2018

(65) Prior Publication Data
US 2019/0314580 A1      Oct. 17, 2019

Related U.S. Application Data

(60) Provisional application No. 62/418,426, filed on Nov. 7, 2016.

(51) Int. Cl.
*A61M 5/315* (2006.01)
*A61M 5/31* (2006.01)
*A61K 31/5513* (2006.01)

(52) U.S. Cl.
CPC ..... *A61M 5/31563* (2013.01); *A61K 31/5513* (2013.01); *A61M 5/3135* (2013.01); *A61M 5/31513* (2013.01); *A61M 5/31551* (2013.01); *A61M 2005/3126* (2013.01); *A61M 2205/582* (2013.01); *A61M 2210/1064* (2013.01)

(58) Field of Classification Search
CPC ............ A61M 5/31563; A61M 5/3135; A61M 5/31513; A61M 5/31551; A61M 5/31561; A61M 5/31511; A61M 5/31525; A61M 5/31528; A61M 5/3155; A61M 2005/3126; A61M 2205/582; A61M 2210/1064
See application file for complete search history.

(56) References Cited

U.S. PATENT DOCUMENTS

| | | | | |
|---|---|---|---|---|
| 2,605,763 | A * | 8/1952 | Smoot ............... | A61M 5/31553 604/70 |
| 4,526,294 | A * | 7/1985 | Hirschmann ......... | G01F 11/023 222/309 |
| 5,462,740 | A | 10/1995 | Evenstad et al. | |
| 5,578,011 | A | 11/1996 | Shaw | |
| 5,632,733 | A | 5/1997 | Shaw | |
| 6,090,077 | A | 7/2000 | Shaw | |

(Continued)

OTHER PUBLICATIONS

DPT Laboratories, Ltd.. Diastat AcuDial Administration and Disposal Instructions, 2016, 8pp., San Antonio, TX.

*Primary Examiner* — Nathan R Price
*Assistant Examiner* — Justin L Zamory
(74) *Attorney, Agent, or Firm* — Elie Gendloff; Gendloff IP

(57) ABSTRACT

A drug delivery system is provided that has an adjustable dose mechanism allowing setting and locking the dose then administration of the set dose. A method for administering a medicament using the drug delivery system is also provided.

20 Claims, 12 Drawing Sheets

(56) References Cited

U.S. PATENT DOCUMENTS

| | | |
|---|---|---|
| 6,572,584 B1 | 6/2003 | Shaw et al. |
| 7,329,241 B2 | 2/2008 | Horvath et al. |
| 7,351,224 B1 | 4/2008 | Shaw |
| 2008/0108952 A1* | 5/2008 | Horvath ............ A61M 5/31548 604/208 |
| 2008/0287883 A1* | 11/2008 | Radmer ............ A61M 5/31548 604/211 |
| 2011/0313396 A1* | 12/2011 | Chanoch ........... A61M 5/31551 604/506 |

\* cited by examiner

ADJUSTABLE DOSE DRUG DELIVERY SYSTEM

CROSS-REFERENCE TO RELATED APPLICATION

This application claims the benefit of U.S. Provisional Application No. 62/418,426, filed Nov. 7, 2016, incorporated by reference herein in its entirety.

BACKGROUND OF THE INVENTION

(1) Field of the Invention

The present application generally relates to drug administration systems. More specifically, systems having an adjustable dose mechanism allowing setting and locking the dose then administration of the set dose.

(2) Description of the Related Art

A system for home administration of a drug has several preferred characteristics. The system should have simple, foolproof procedures for administering the drug. The system also preferably has a dosage adjustment mechanism that allows for the dosage to be set depending on the needs of the patient. The system can also have a mechanism allowing the set dosage to be locked, e.g., by a pharmacist. See U.S. Pat. Nos. 5,462,740; 5,578,011; 5,632,733; 6,090,077; 6,572,584; 7,329,241; and 7,351,224.

Provided is a drug delivery system having the above characteristics.

BRIEF SUMMARY OF THE INVENTION

Provided herewith is an adjustable dose drug delivery system comprising:

a plunger, a syringe body, an inner housing, a plunger sleeve, an outer housing, and a rotating collar, wherein the plunger comprises a stopper at a distal end, a plunger flange comprising a center at a proximal end, and a plunger stem fixed to the center of the plunger flange at the proximal end;

the syringe body comprises a syringe tip at a distal end and an open proximal end comprising a syringe body flange, wherein the plunger is slidably deposed by inserting the stopper into the open proximal end of the syringe body and pushing the plunger flange toward the syringe body distal end;

the inner housing comprises a proximal end and a distal end and encloses the syringe body and is affixed thereto, wherein the inner housing further comprises a plurality of dosage stops spirally deposed between the inner housing proximal end and distal end;

the plunger sleeve is distal to the plunger flange, and has a circumference within a plunger flange circumference and distal thereto, and encloses, and is external to, the plunger stem, and is deposed outside the inner housing and, when pushed toward the syringe body distal end, slides along the inner housing toward the plurality of dosage stops, wherein the plunger sleeve further comprises
a closed slot running parallel to the plunger stem, and
a dosage stop engagement mechanism that engages a dosage stop when the plunger sleeve slides along the inner housing, said engagement preventing (a) further sliding of the plunger sleeve along the inner housing and (b) further insertion of the plunger toward the syringe body distal end;

the outer housing encompasses the inner housing and comprises a proximal end overlapping and deposed outside the plunger sleeve; and the rotating collar surrounds the plunger sleeve and the proximal end of the outer housing and is rotationally joined to the plunger sleeve by a pin inserted into the plunger sleeve closed slot, wherein the rotating collar further comprises a window displaying dosage information present on the outer housing, and
rotating the rotating collar displays a series of specific dosages in the window and rotates the plunger sleeve to align the dosage stop engagement mechanism to a dosage stop on the inner housing corresponding to the specific dosage displayed in the window.

Also provided is an adjustable dose drug delivery system comprising:

a plunger, a syringe body, an inner housing, a plunger sleeve, an outer housing, a rotating collar and a locking collar, wherein the plunger comprises a stopper at a distal end, a plunger flange comprising a center at a proximal end, and a plunger stem fixed to the center of the plunger flange at the proximal end;

the syringe body is glass and comprises a syringe tip at a distal end and an open proximal end comprising a syringe body flange, wherein the plunger is slidably deposed by inserting the stopper into the open proximal end of the syringe body and pushing the plunger flange toward the syringe body distal end;

the inner housing comprises a proximal end and a distal end and encloses the syringe body and is affixed thereto, wherein the inner housing further comprises a plurality of dosage stops spirally deposed between the inner housing proximal end and distal end;

the plunger sleeve is distal to the plunger flange, and has a circumference within a plunger flange circumference and distal thereto, and encloses, and is external to, the plunger stem, and is deposed outside the inner housing and, when pushed toward the syringe body distal end, slides along the inner housing toward the plurality of dosage stops, wherein the plunger sleeve further comprises
a closed slot running parallel to the plunger stem, and
a dosage stop engagement mechanism that engages a dosage stop when the plunger sleeve slides along the inner housing, said engagement preventing (a) further sliding of the plunger sleeve along the inner housing and (b) further insertion of the plunger toward the syringe body distal end, wherein the dosage stop engagement mechanism comprises
an inwardly directed locking finger at the distal end of the plunger sleeve engaging an outwardly directed knob at the dosage stop,
and an outwardly and distally directed ramp proximal to the knob, with a gap between the ramp and the knob so that the locking finger ascends the ramp and drops into the gap when the plunger sleeve moves distally along the inner housing to the dosage stop corresponding to the dosage indicated in the window;

the outer housing encompasses the inner housing and comprises a proximal end overlapping and deposed outside the plunger sleeve;

the rotating collar surrounds the plunger sleeve and the proximal end of the outer housing and is rotationally joined to the plunger sleeve by a pin in the rotating collar inserted into the plunger sleeve closed slot, wherein the rotating collar further comprises a window displaying dosage information present on the outer housing, and rotating the rotating collar displays a series of specific dosages in the window and rotates the plunger sleeve to align the dosage stop engagement mechanism to a dosage stop on the inner housing corresponding to the specific dosage displayed in the window;

the locking collar surrounds the plunger sleeve and the proximal end of the outer housing adjacent to the rotating collar and rotationally joined thereto, wherein the rotating collar is initially separated from the locking collar by a gap, wherein closing the gap engages a locking mechanism preventing rotation of the rotating collar and plunger sleeve, wherein the locking mechanism comprises inwardly directed tabs on the locking collar nearest to the outer housing engaging notches in the outer housing at the position of each dosage stop;

the system further comprising an initial stop mechanism preventing, without rotating the rotating collar to display dosage information, (i) sliding of the plunger sleeve along the inner housing toward the plurality of stops and (ii) insertion of the plunger toward the syringe body distal end, wherein the initial stop mechanism is (A) a protrusion on the inner housing above the dosage stops, and (B) open slots in the plunger sleeve extending from near the proximal end and opening at the distal end of the plunger sleeve, where the open slots align with the protrusion when the rotating collar is rotated to display a specific dosage in the window allowing the plunger and the plunger sleeve to slide to the dosage stop corresponding to the dosage displayed.

Additionally provided is a method of administering a medicament to a patient. The method comprises administering the medicament using the drug delivery system of any one of claims 1-18, wherein the medicament is initially inside the syringe body and a dosage of the medicament is administered through the distal end of the syringe body or outer housing.

BRIEF DESCRIPTION OF THE DRAWINGS

In accordance with the present invention.

DETAILED DESCRIPTION OF THE INVENTION

Figure 1A:
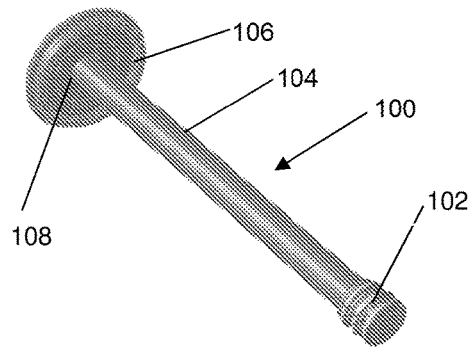
FIG. 1A is a perspective view of a plunger.

As used herein, the singular forms "a", "an" and "the" are intended to include the plural forms as well, unless the context clearly indicates otherwise. Additionally, the use of "or" is intended to include "and/or", unless the context clearly indicates otherwise.

In the description that follows, like parts will be referred to by the same reference numerals. Parts with a lowercase letter are mean to illustrate a minor variation of a part with the same number.

Figure 1B:
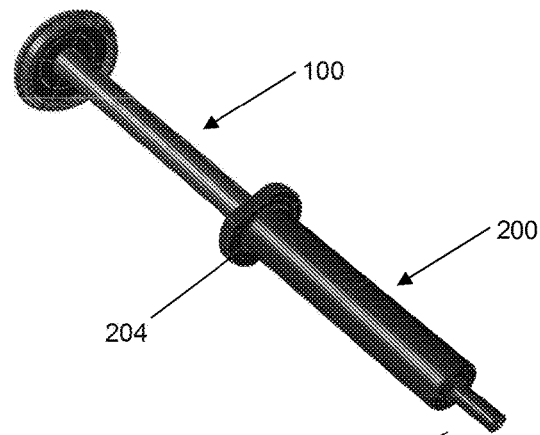
FIG. 1B is a perspective view of a plunger inserted into a syringe body.

FIGS. 1A-I show an embodiment of the basic components of the drug delivery system of the present invention. FIG. 1A shows a plunger 100 comprising a stopper 102, a plunger stem 104, a plunger flange 106 comprising a center 108, where the proximal end of the plunger stem is fixed. The plunger in these embodiments is generally typical of conventional syringe plungers, as illustrated in FIG. 1B, serving to be slidably deposed into a syringe body 200 open proximal end adjacent to a syringe body flange 204 where a drug present in the syringe body 200 may be injected through a syringe tip 202 by pushing the plunger flange toward the syringe body distal end, adjacent to a syringe tip 202.

Figure 1C:
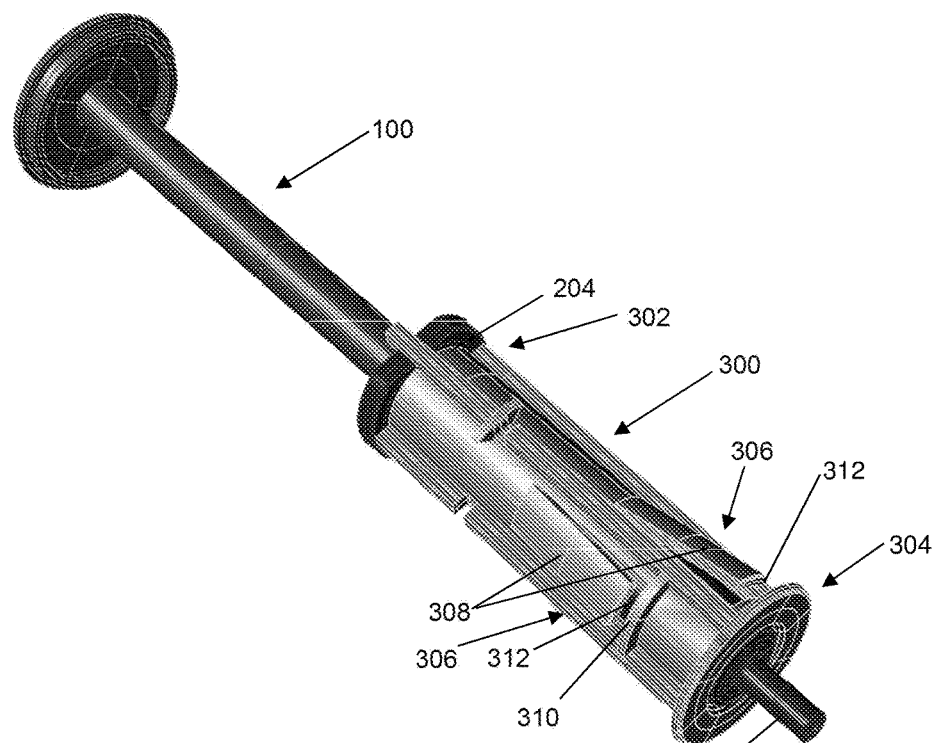
FIG. 1C is a perspective view of an inner housing encompassing a syringe body with a plunger inserted therein.

FIG. 1C shows an inner housing 300 enclosing a syringe body 200 leaving a syringe body flange 204 and a syringe tip 202 exposed. A plunger 100 inserted into the syringe body is also shown.

The inner housing comprises a proximal end 302 and a distal end 304 and encloses the syringe body and is affixed thereto. In alternative embodiments, the inner housing and syringe body are one piece, as exemplified as inner housing 300a in FIGS. 4A-5C.

The inner housing further comprises a plurality of dosage stops 306 spirally deposed between the inner housing proximal end 302 and distal end 304. In various embodiments, the dosage stops are comprised of a ramp 308, a knob 310 and a gap 312, further discussed below.

Figure 1D:
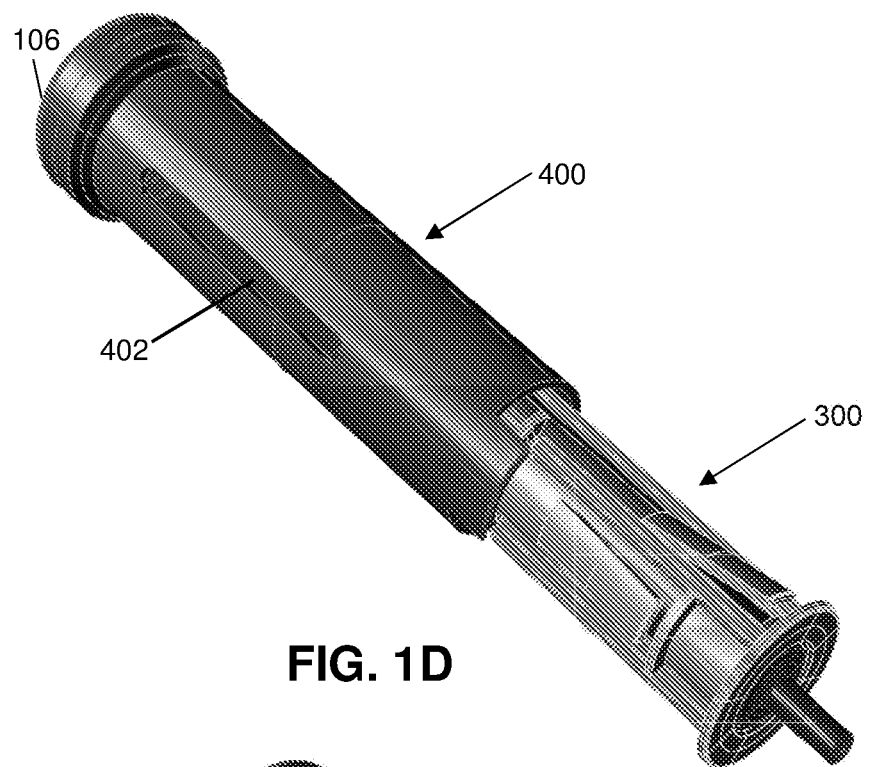
FIG. 1D is a perspective view of a plunger sleeve encompassing a plunger and overlapping an inner housing.

FIG. 1D shows a plunger sleeve 400 distal to the plunger flange 106. The plunger sleeve 400 has a circumference within the circumference of the plunger flange distal thereto, and encloses, and is external to, the plunger stem (not shown), and is deposed outside the inner housing 300 and, when pushed toward the syringe body distal end, slides along the inner housing toward the plurality of dosage stops. The plunger sleeve further comprises a closed slot 402 running parallel to the plunger stem, and a dosage stop engagement mechanism (not shown) that engages a dosage stop when the plunger sleeve slides along the inner housing, said engagement preventing (a) further sliding of the plunger sleeve 400 along the inner housing 300 and (b) further insertion of the plunger toward the syringe body distal end.

Figure 1E:
FIG. 1E is a perspective view of an outer housing overlapping a plunger sleeve.

FIG. 1E shows an outer housing 500 that encompasses the inner housing (not shown) and comprises a proximal end 502 overlapping and deposed outside the plunger sleeve 400. The outer housing in these embodiments further comprise an administration tip 506 through which the drug is administered.

Figure 1F:
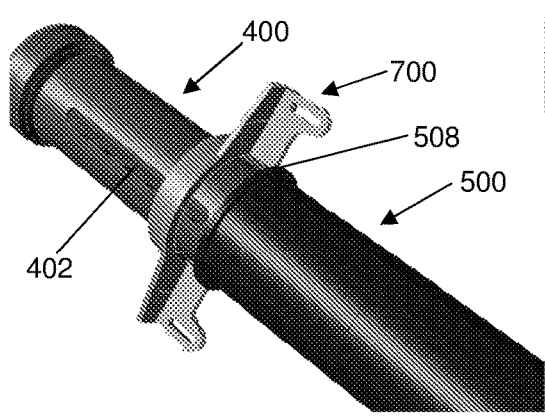
FIG. 1F is a perspective view of a locking collar encircling a plunger sleeve, which is partially inserted into an outer housing.

FIG. 1F shows a locking collar 700 surrounding the plunger sleeve 400 and the proximal end of the outer housing 500. In some embodiments, the proximal end of the outer housing 500 as notches 508 that the locking collar 700 engages when a dosage lock mechanism is engaged.

Figure 1G:
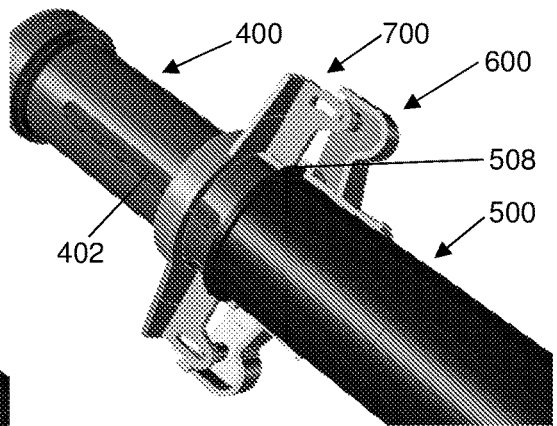
FIG. 1G is the perspective view of FIG. 1F with a cutaway of a rotating collar.

FIG. 1G shows a rotating collar 600 that surrounds the plunger sleeve 400 and the proximal end of the outer housing 500 and is rotationally joined to the plunger sleeve by a pin inserted into the plunger sleeve closed slot 402. The locking collar 700 is adjacent to the rotating collar and rotationally joined thereto.

Figure 1H:
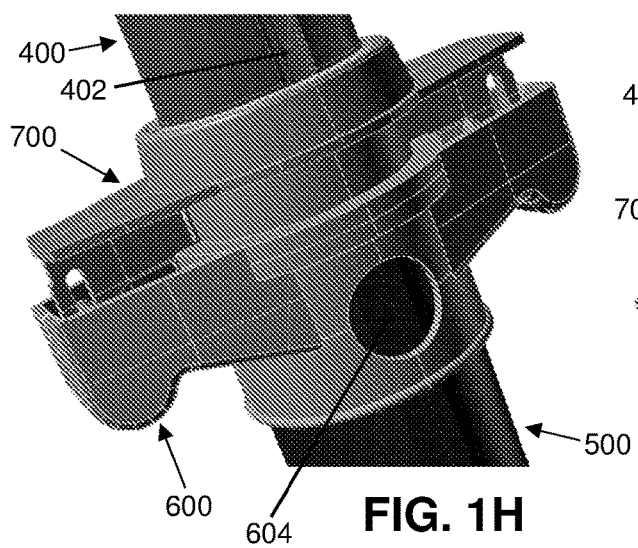
FIG. 1H is a perspective view of a rotating collar, a locking collar, and portions of a plunger sleeve and outer housing.
Figure 1I:
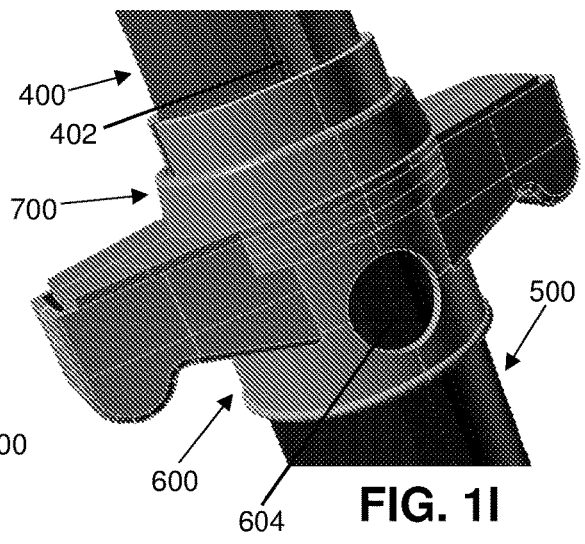
FIG. 1I is the perspective view of FIG. 1H, with the locking collar locked with the rotating collar.

FIG. 1H shows a close-up of the rotating collar 600 and the locking collar 700 in the unlocked position. In that position, the rotating collar 600 is separated from the locking collar 700 by a gap. The rotating collar 600 further comprises a window 604 displaying dosage information present on the outer housing 500. In practice, rotating the rotating collar 600 displays a series of specific dosages in the window 604 and rotates the plunger sleeve 400 to align the dosage stop engagement mechanism (not shown) on the plunger sleeve 400 to a dosage stop on the inner housing not shown) corresponding to the specific dosage displayed in the window 604.

After the dosage is selected, the gap between the rotating collar 600 and the locking collar 700 may be closed, which prevents additional rotation of the rotating collar 600, thus locking the dosage setting. Any mechanism may be used to prevent that additional rotation when the gap is closed between the rotating collar 600 and the locking collar 700. In some embodiments, further described below, the locking collar 700 engages with the notches 508 at the proximal end of the outer housing 500.

The pin (not shown in FIG. 1) that joins the rotating collar 600 to the plunger sleeve 400 may be on the rotating collar 600 or the locking collar 700.

Figure 2A:
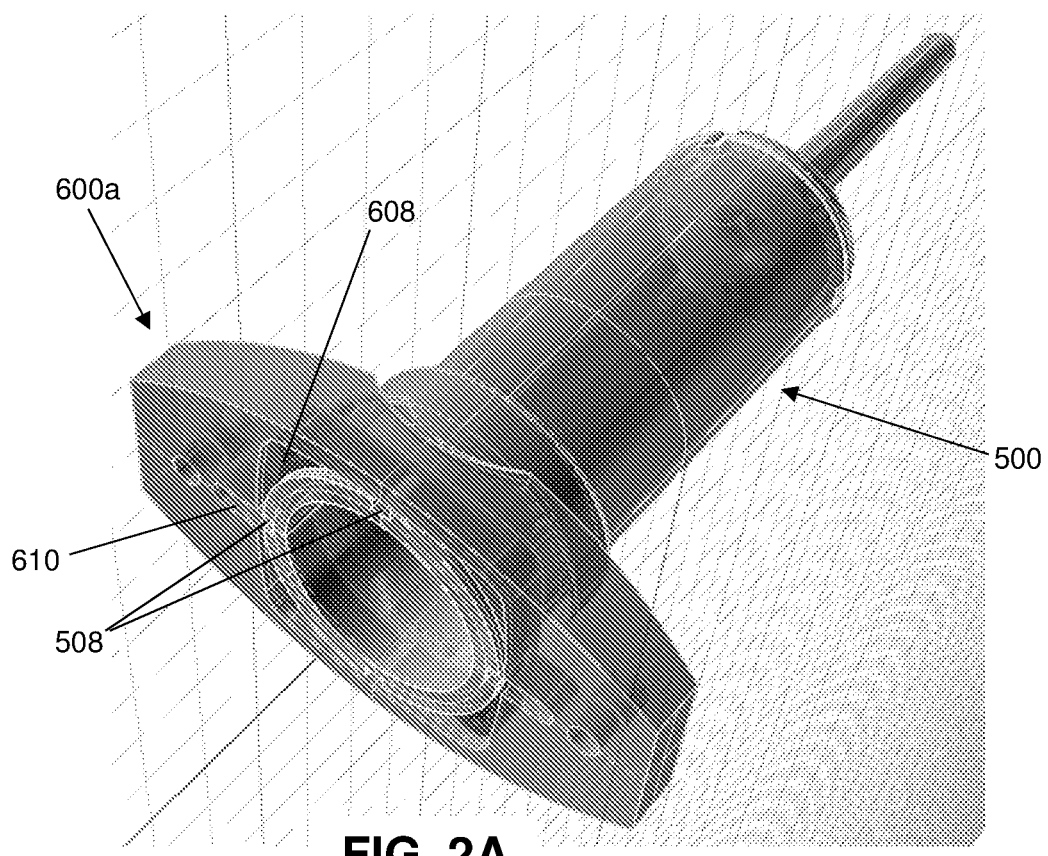
FIG. 2A is a transparent view of a rotating collar encircling the outer housing, with detents.
Figure 2B:
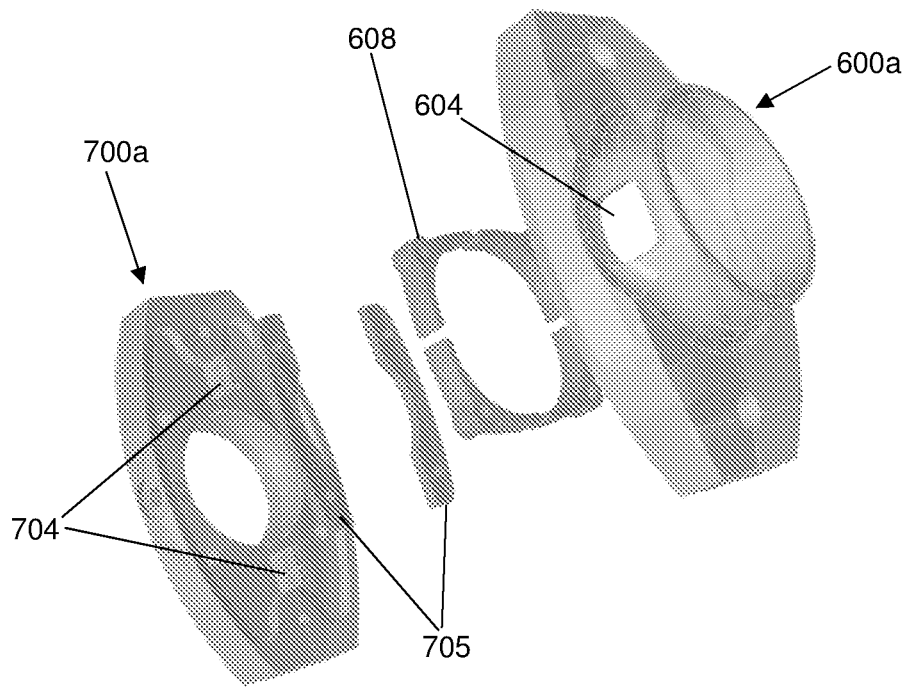
FIG. 2B is an exploded view of a rotating collar, a locking collar, detents, and gaskets.
Figure 2C:
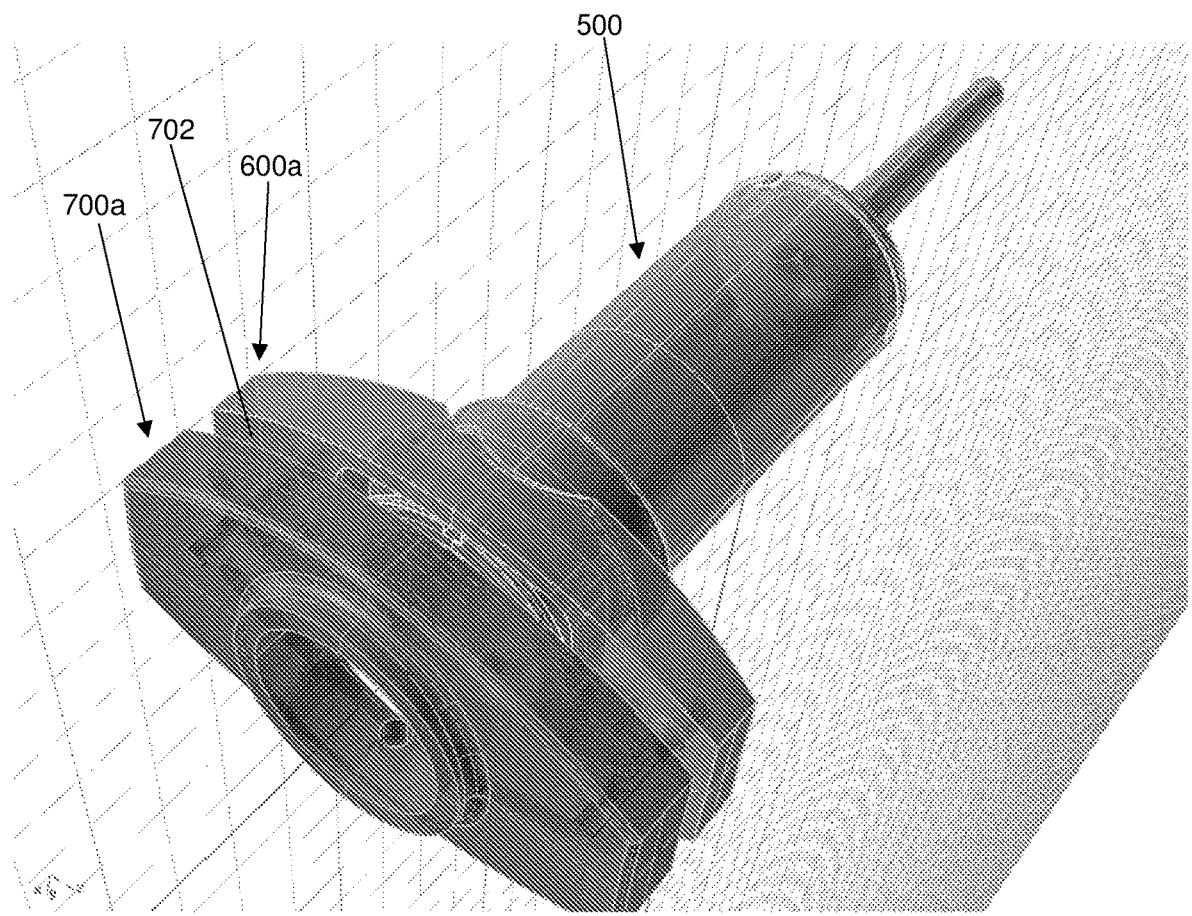
FIG. 2C is the transparent view of FIG. 2A with a locking collar.
Figure 3A:
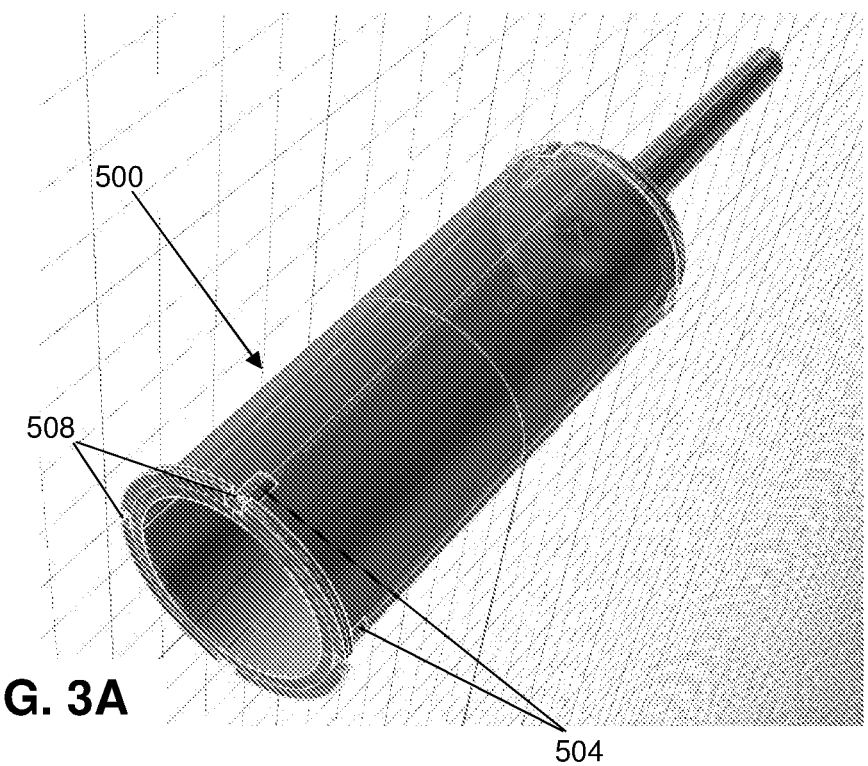
FIG. 3A is a transparent view of an outer housing.
Figure 3B:
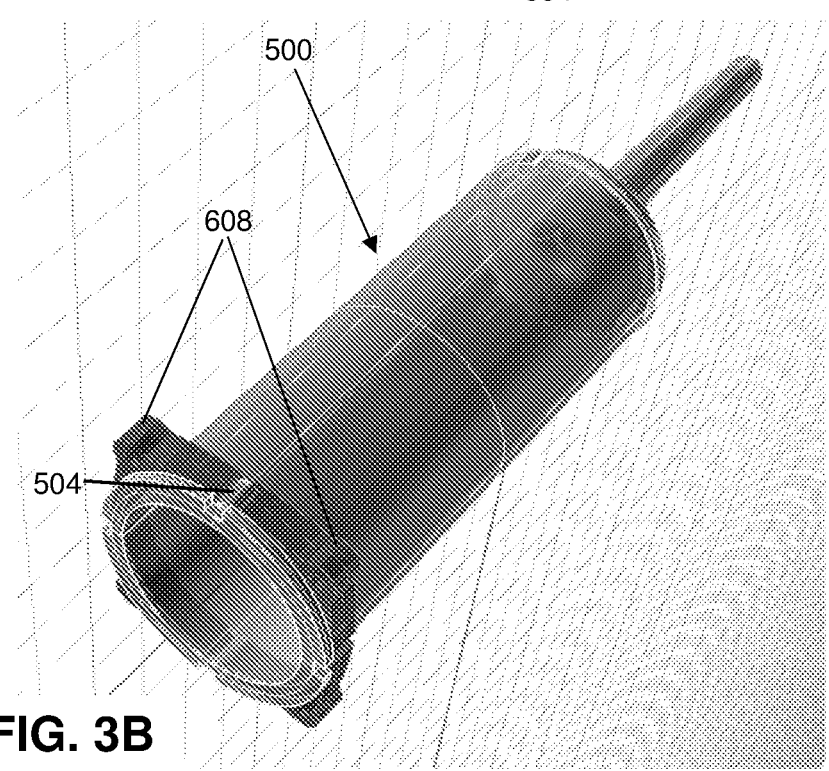
FIG. 3B is the transparent view of FIG. 3A, with detents.

FIGS. 2A, 2B and 2C show an alternative embodiment of a rotating collar 600a and a locking collar 700a. The rotating collar 600a shows slots 610 that align with notches 508 in the outer housing. The slots 610 and notches 508 align with inwardly directed tabs 704 on the locking collar 700a. In practice, the rotating collar 600a is rotated to display the desired dose in the window 604, after which the gap between the rotating collar and the locking collar 702 is closed, causing the inwardly directed tabs 704 to engage the slots 610 and adjacent notches 508. This prevents further rotation of the rotating collar 600a since the inwardly directed tabs 704 is inserted into the notches 508, preventing movement relative to the outer housing 500.

In some embodiments, the drug delivery system also comprises a removable insert between the rotating collar and the locking collar that prevents closing the gap. Such an insert prevents accidental locking of the rotating collar and locking collar, e.g., during shipping, and can have any form. The drug delivery system can also have a mechanism to prevent pulling apart the locking collar and rotating collar after locking (closing the gap). Such a mechanism can have any form known in the art.

FIGS. 2A, 2B, 3A and 3B also show embodiments having detents 608 fitting into a recess in the rotating collar 600a. The detents 608 engage the rotating collar 600a and the proximal end of the outer housing 500 with gaps in the detents 608 that align with shallow protrusions 504 in the outer housing 500 to reversibly stop the rotation at the dosage information displays. The detents 608 are made from a resilient material, e.g., a plastic, such that, when the rotating collar 600a is rotated between dosage settings, the detents 608 move over the shallow protrusions 504, causing some resistance to the rotating action. When the rotating collar 600a is further rotated to where a dosage is displayed in the window 604, the gap in the detents 608 aligns with the shallow protrusions 504 causing a haptic signal to the operator that the system is properly aligned to the selected dose displayed in the window 604.

FIG. 2B also shows gaskets 705, which may be used to prevent further movement of the detents 608 when the gap is closed and the rotating collar 608a cannot be further rotated.

FIGS. 4A, 4B, 4C, 5A, 5B and 5C shows additional embodiments where the inner housing 300a is combined with the syringe body as one piece. Additionally, in these embodiments, an administration tip 318 is present at the distal end of the inner housing 300a, unlike the embodiments illustrated in FIGS. 1E, 2A-2C 3A and 3B, where the administration tip 506 is at the distal end of the outer housing 500a. Unlike the outer housing 500 shown in FIGS. 1E, 2A, 2C, 3A and 3B, the outer housing 500a does not comprise an administration tip, since that is supplied on the inner housing 300a.

Figure 4A:
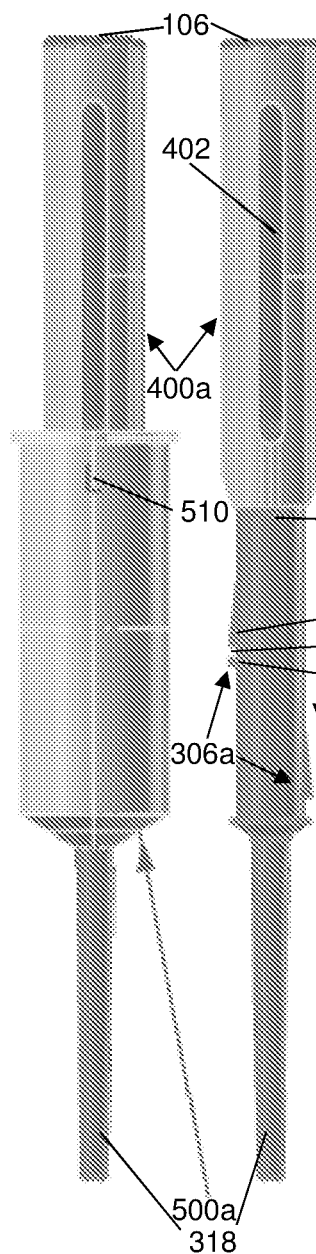
FIG. 4A is a perspective view of a plunger sleeve with an outer housing on the left, and a plunger sleeve with an inner housing on the right.
Figure 4B:
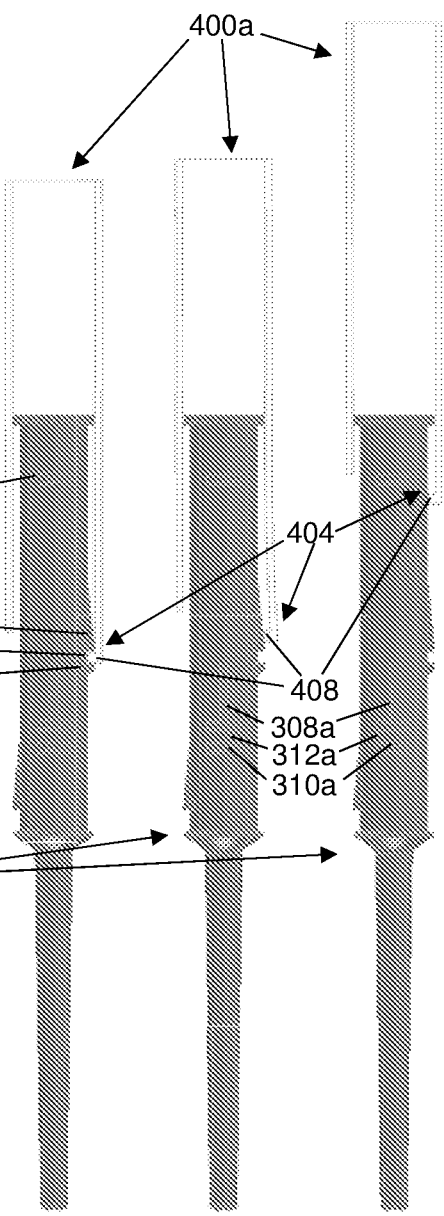
FIG. 4B is a sequential series of a perspective view of an inner housing and a cross-section of a plunger sleeve before injection (right), during injection (center), and after injection (left) of the lowest dose provided in the system.
Figure 4C:
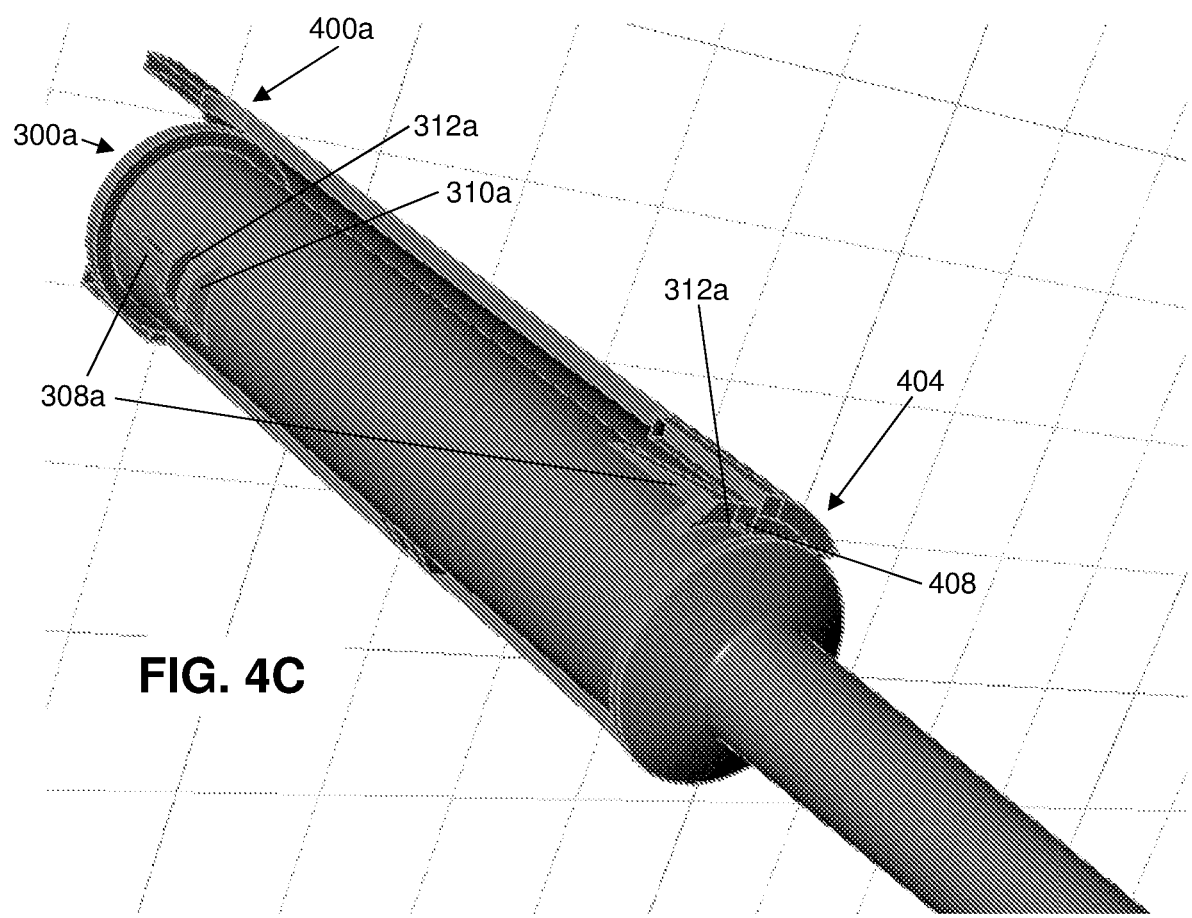
FIG. 4C is a perspective view of an inner housing and a cutaway view of a plunger sleeve after the highest dose provided in the system has been administered.

FIG. 4A shows a plunger sleeve 400a, plunger flange 106, and (left) outer housing 500 or (right) inner housing 300a at the initial "locked" position, indicated by the "L" display 510 on the outer housing. The inner housing 300a has an initial stop mechanism comprising a protrusion 314 that engages with an inwardly directed locking finger 408, shown in FIGS. 4B, 5A, 5B and 5C. In the initial locked position (FIGS. 4A and 5B), the plunger sleeve 400a is prevented from being pushed downward to dispense a drug by the locking finger 408 engagement with the protrusion 314. The initial stop mechanism can be a simple protrusion or it can be the same structure as a dosage stop, having a ramp 308a, a knob 310a and a gap 312a, as shown in FIG. 4C, near the top of the inner sleeve 300a.

When the rotating collar (not shown) is rotated to a specific dosage, the plunger sleeve 400a turns, by virtue of the pin in the rotating collar engaging the closed slot 402 in the plunger sleeve, moving the locking finger 408 away from the protrusion 314 to align with a dosage stop 306a corresponding to the dosage displayed. When the plunger flange 106 is then pushed downward, the plunger sleeve 400a also moves downward (FIG. 4B), until the locking finger 408 engages with the dosage stop 306a for the selected dosage. In that engagement, the locking finger slides up the ramp 308a and enters the gap 312a where it is prevented from further downward movement by the knob 310a, or upward movement by the ramp 308a, as shown in FIG. 4C, depicting an inner housing 300a and a plunger sleeve 400a after the highest dosage was set and administered. In FIG. 4C, the locking finger 408 (the dosage stop engagement mechanism 404 for the illustrated embodiments) is in the gap 312a of the dosage stop for the highest dosage. In that embodiment, there is no knob in the dosage stop for the highest dosage, since the dosage stop is at the bottom of the inner housing, where the plunger is at the end of the syringe body.

Figure 5A:
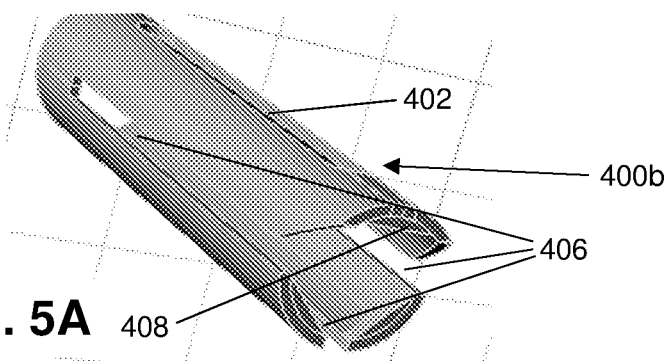
FIG. 5A is a perspective view of a plunger sleeve.
Figure 5B:
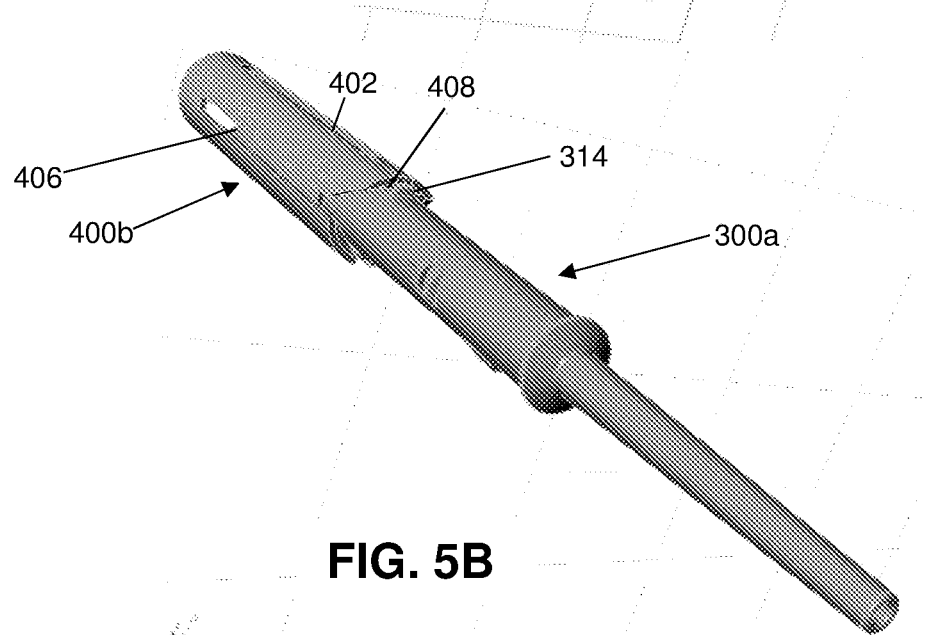
FIG. 5B is a perspective view of a plunger sleeve engaged with an inner housing at the locked initial position.
Figure 5C:
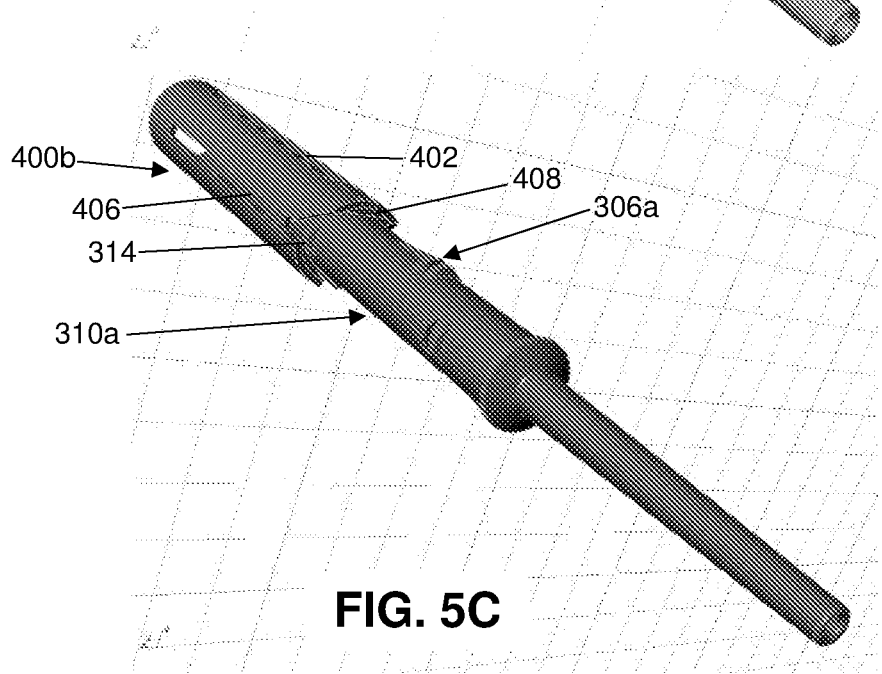
FIG. 5C is a perspective view of a plunger sleeve engaged with an inner housing at the lowest dose position, before injection.

FIGS. 5A, 5B and 5C show an embodiment where a plunger sleeve 400b has open slots 406 that provide for the protrusion 314 when the dosage is set at each dosage setting. In these embodiments, the protrusion 314 otherwise prevents movement of the plunger sleeve 400b downward. This mechanism prevents administration of a dosage when the dosage is not properly set.

FIG. 5B shows the plunger sleeve 400b and inner housing 300a at the initial locked dosage position. The locking finger 408 is prevented from moving due to the blockage from the protrusion 314. In these embodiments, the protrusion 314 is also a knob 310a, as shown in FIG. 4C. Because the locking finger 408 is in the gap 312a between a knob 310a and a ramp 308a, the plunger is unable to be pushed downward or retracted. At this initial setting, the protrusion 314 is aligned with the closed slot 402.

FIG. 5C shows the plunger sleeve 400b and inner housing 300a at the lowest dosage setting, before administration of the drug. In that position, the protrusion 314 is aligned with an open slot 406, allowing administration of the dose, since the protrusion 314 is not blocking the downward movement of the plunger sleeve 400b. The locking finger 408 is aligned with the dosage stop 306a corresponding to the lowest dosage.

Figure 5D:
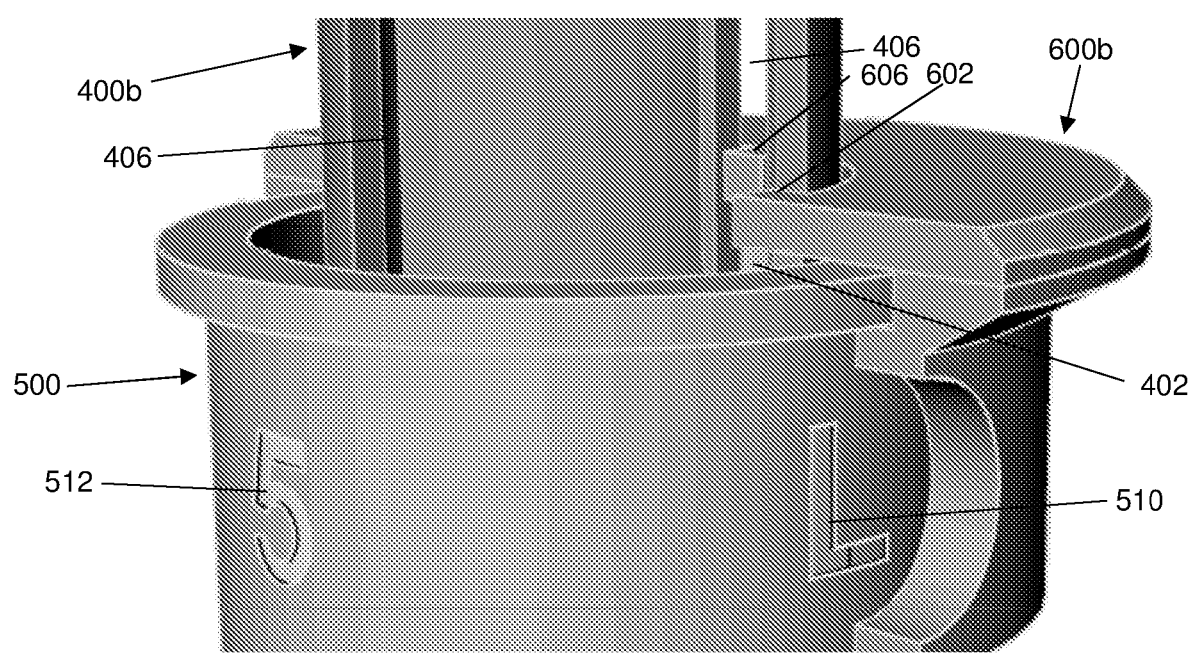
FIG. 5D is a perspective view of a plunger sleeve and the top of an outer housing, with a cutaway of a rotating collar.

In some embodiments, as shown in FIG. 5D, the rotating collar 600b further comprises protrusions 606 that are inserted into the open slots 406 of the plunger sleeve 400b. FIG. 5D shows an alternative design of the rotating collar 600b, the locked dosage display 'L' 510 a '5' dosage display 512 on the outer housing 500, and the pin 602 in the closed slot 402. In these embodiments, the pin 602 in the closed slot 402 are aligned with the locked dosage display 'L' 510.

Figure 6:
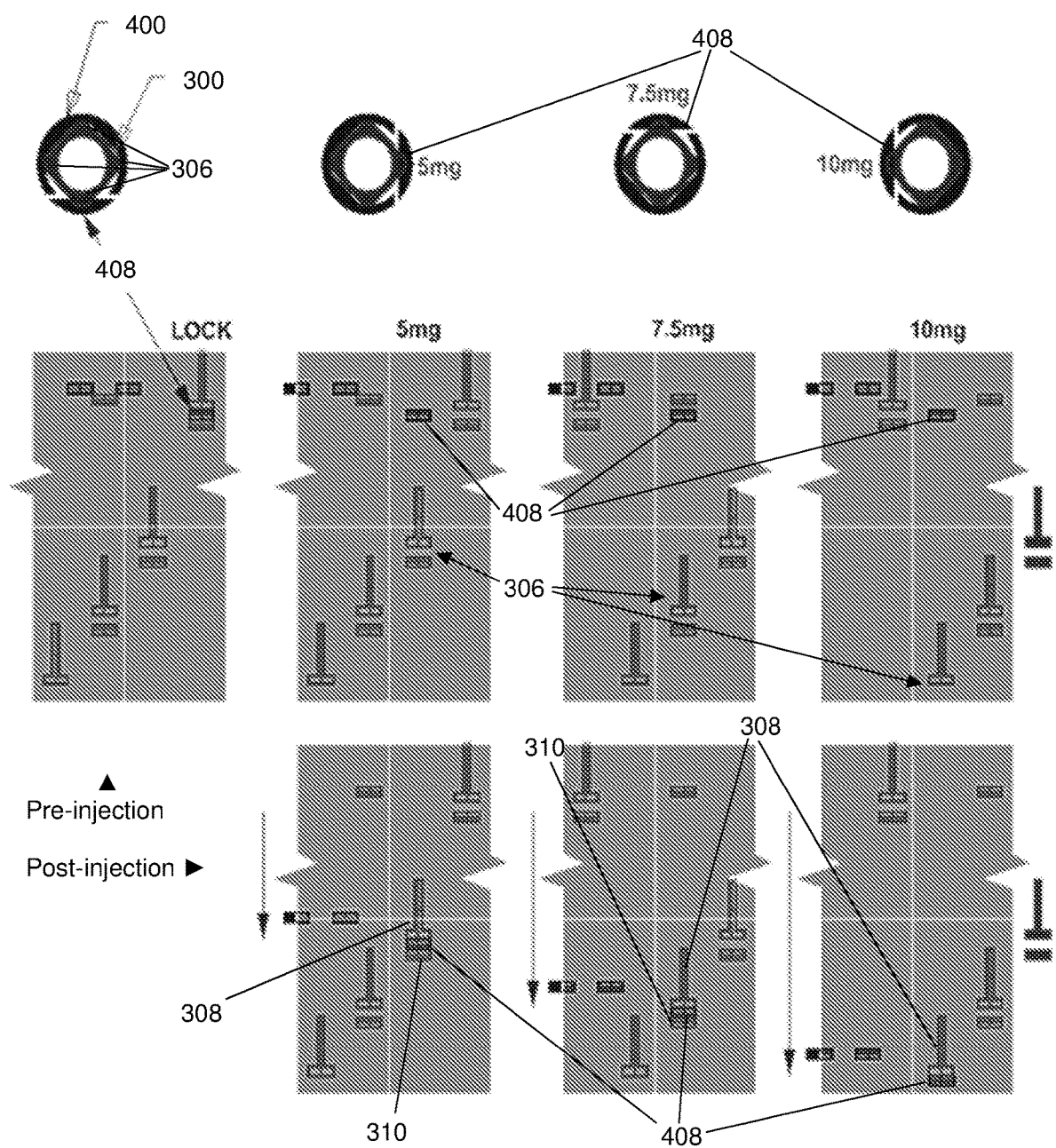
FIG. 6 is cross-sectional views of a plunger sleeve and inner housing at an initial lock position and three dose positions provided in the system (top), and flattened views of an inner housing at those positions before (middle) and after (bottom) injection.

FIG. 6 shows cross-sections of a plunger sleeve 400 and inner housing 300 at the (left to right) locked, 5 mg, 7.5 mg and 10 mg dosage settings (top), and flattened views of (a) the inner housing at those settings pre-injection (middle) and (b) the three dosage settings post-injection (bottom). The position of the locking finger 408 at each dosage level is indicated, as is the corresponding dosage stop 306, where the locking finger resides after administration (bottom).

Figure 7:
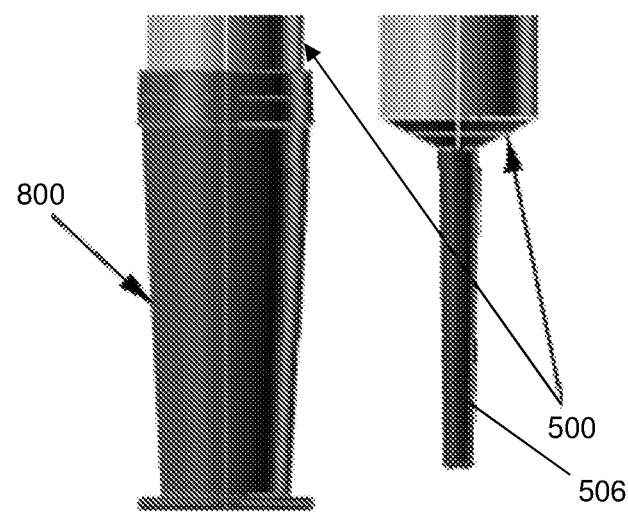
FIG. 7 is a perspective view of a portion of an outer housing and a cap (left) and the outer housing without the cap.

In some embodiments, e.g., as shown in FIG. 7, a cap 800 covers the distal portion of the outer housing as well as the administration point, e.g., an administration tip, e.g., 318 or 506, at the distal end of the inner housing 300a or outer housing 500, respectively, a needle, or any other administration point. The cap 800 is useful to protect the administration point (e.g., administration tip or needle), and would be removed prior to administration of the drug.

Figure 8:
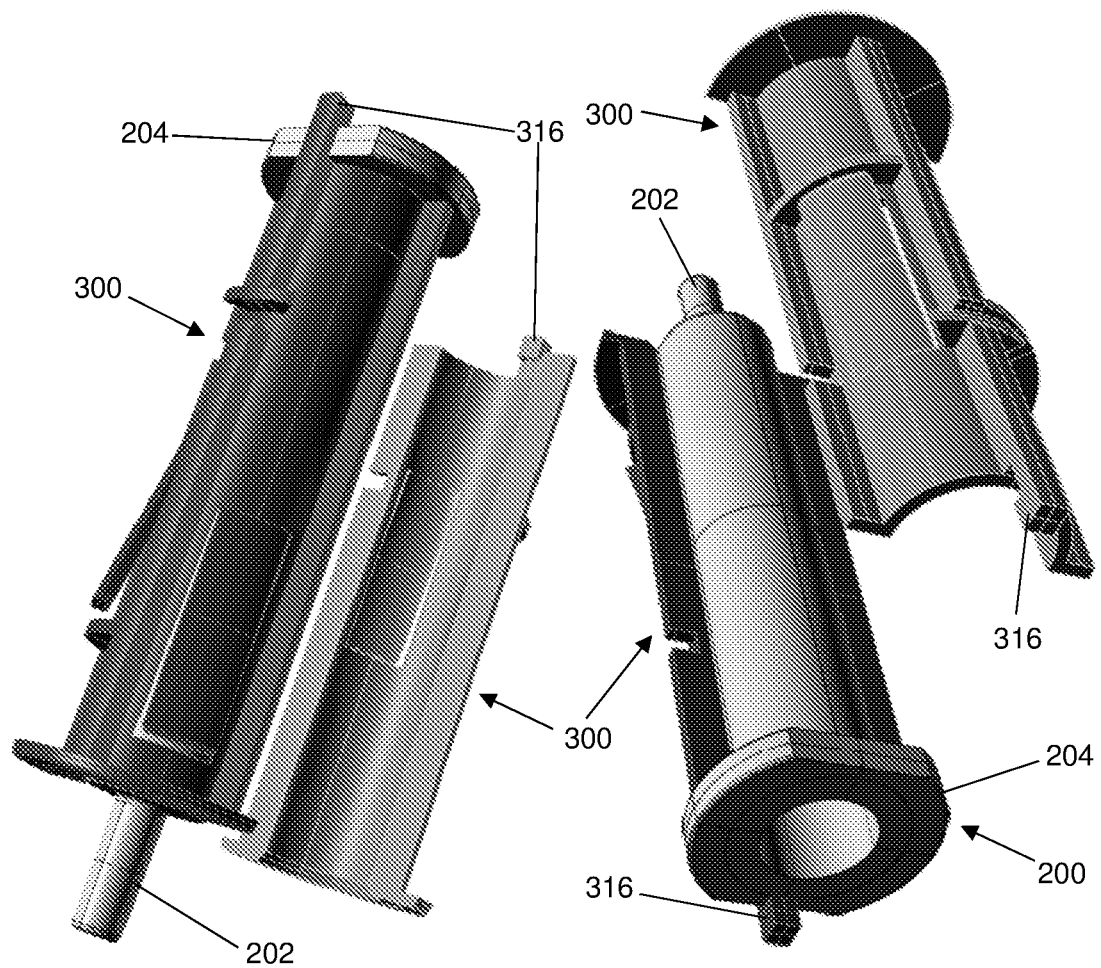
FIG. 8 is an exploded view of an inner housing and syringe body.

As previously discussed, e.g., in relation to the embodiments illustrated in FIGS. 1C, 1D and 8, the syringe body 200 and inner housing 300 are separate parts. The syringe body can be specifically designed for these embodiments, or a commercial syringe body can be used. Any commercial syringe body can be used, made of, e.g., glass or plastic as is known in the art, e.g., a HYPAK glass syringe. FIG. 8 shows a way that an inner housing 300 can be supplied as two parts, each with a hook 306 that hooks onto a standard commercial syringe body such as a HYPAK glass syringe.

Although 5 mg, 7.5 mg, and 10 mg dosages are exemplified above, the drug delivery system of the present invention can utilize any dosage level of any drug, in any formulation. Additionally, although only three dosages are provided in the exemplified embodiments, the system can provide for at least two, four, five, six or more dosages.

Although the illustrated embodiments provide for a long administration tip 318 or 506, which are particularly suitable for anal administration, the system of the present invention is also suitable to be used with needles, e.g., attached to the syringe tip 202 as in FIG. 1D. The needle could be used for any administration that uses a needle, e.g., intravenous, subdermal, intramuscular, intraperitoneal, etc. Thus, an alternative outer housing for the partial system illustrated in FIG. 1D, is the outer housing 500a in the embodiment illustrated in FIG. 4A, since that outer housing 500a does not have an administration tip. The partial device of FIG. 1D with the outer housing 500a could then accommodate a needle or an alternative administration means, e.g., for intranasal, oral, sublingual, buccal, ophthalmic, infusion, topical, enteric, inhaled, or transdermal administration, as those administration means are known in the art.

In certain specific embodiments, the drug delivery system has an administration tip suitable for rectal administration, and the drug is a benzodiazepine, for example diazepam. Such a system is suitable for treatment of, e.g., epilepsy.

The present invention is also directed to a method of administering a medicament to a patient. The method comprises administering the medicament using the drug delivery system described above. In these embodiments, the medicament is initially inside the syringe body and a dosage of the medicament is administered through the distal end of the syringe body or outer housing.

Some embodiments of these methods further comprise rotating the rotating collar and plunger sleeve until a desired dosage appears in the window of the rotating collar, applying a distal end of the system to an administration point of the patient, and pushing the plunger and plunger sleeve until the dosage stop engagement mechanism engages the dosage stop corresponding to the desired dosage.

The rotating collar may be rotated by a pharmacist, a patient, a caregiver, a physician, a nurse, or any other individual participating in the usage of the system. In some embodiments, a pharmacist rotates the rotating collar and plunger sleeve until the desired dosage appears, and a patient or caregiver applies a distal end of the system and pushes the plunger and plunger sleeve until the dosage stop is engaged. Where a locking collar is present, the pharmacist would also engage the locking mechanism by bringing the locking collar together with the rotating collar.

In some of these embodiments, the medicament is administered rectally. In some of those embodiments, the medicament is a benzodiazepine, for example diazepam. In certain of those embodiments, the patient has been diagnosed with epilepsy.

In view of the above, it will be seen that several objectives of the invention are achieved and other advantages attained.

As various changes could be made in the above methods and compositions without departing from the scope of the invention, it is intended that all matter contained in the above description and shown in the accompanying drawings shall be interpreted as illustrative and not in a limiting sense.

All references cited in this specification are hereby incorporated by reference. The discussion of the references herein is intended merely to summarize the assertions made by the authors and no admission is made that any reference constitutes prior art. Applicants reserve the right to challenge the accuracy and pertinence of the cited references.

What is claimed is:

1. An adjustable dose drug delivery system comprising:
   a plunger, a syringe body, an inner housing, a plunger sleeve, an outer housing, and a rotating collar, wherein
   the plunger comprises a stopper at a distal end, a plunger flange comprising a center at a proximal end, and a plunger stem fixed to the center of the plunger flange at a proximal end;
   the syringe body comprises a syringe tip at a distal end and an open proximal end comprising a syringe body flange,
   wherein the plunger is slidably deposed by inserting the stopper into the open proximal end of the syringe body and pushing the plunger flange toward the syringe body distal end;
   the inner housing comprises a proximal end and a distal end and encloses the syringe body and is affixed thereto,
   wherein the inner housing further comprises a plurality of dosage stops spirally deposed between the inner housing proximal end and distal end;
   the plunger sleeve is distal to the plunger flange, and has a circumference within a plunger flange circumference and distal thereto, and encloses, and is external to, the plunger stem, and is deposed outside the inner housing and, when pushed toward the syringe body distal end, slides along the inner housing toward the plurality of dosage stops,
   wherein the plunger sleeve further comprises
   a closed slot running parallel to the plunger stem, and
   a dosage stop engagement mechanism that engages a dosage stop when the plunger sleeve slides along the inner housing, said engagement preventing (a) further sliding of the plunger sleeve along the inner housing and (b) further insertion of the plunger toward the syringe body distal end;
   the outer housing encompasses the inner housing and comprises a proximal end overlapping and deposed outside the plunger sleeve; and
   the rotating collar surrounds the plunger sleeve and the proximal end of the outer housing and is rotationally joined to the plunger sleeve by a pin inserted into the plunger sleeve closed slot, wherein
   the rotating collar further comprises a window displaying dosage information present on the outer housing, and
   rotating the rotating collar displays a series of specific dosages in the window and rotates the plunger sleeve to align the dosage stop engagement mechanism to a dosage stop on the inner housing corresponding to the specific dosage displayed in the window.

2. The drug delivery system of claim 1, further comprising a locking collar surrounding the plunger sleeve and the proximal end of the outer housing adjacent to the rotating collar rotationally joined thereto, wherein the pin is on the rotating collar or locking collar and
   the rotating collar is initially separated from the locking collar by a gap, wherein closing the gap engages a locking mechanism preventing rotation of the rotating collar and plunger sleeve.

3. The drug delivery system of claim 2, wherein the locking mechanism comprises inwardly directed tabs on the locking collar nearest to the outer housing engaging (a) slots in the rotating collar and (b) notches in the outer housing at the position of each dosage stop.

4. The drug delivery system of claim 2, further comprising a removable insert between the rotating collar and the locking collar that prevents closing the gap.

5. The drug delivery system of claim 1, further comprising an initial stop mechanism preventing, without rotating the rotating collar to display dosage information, (i) sliding of the plunger sleeve along the inner housing toward the plurality of stops and (ii) insertion of the plunger toward the syringe body distal end.

6. The drug delivery system of claim 5, wherein the initial stop mechanism is (A) a protrusion on the inner housing above the dosage stops and below the plunger sleeve, and (B) open slots in the plunger sleeve extending from near the proximal end and opening at the distal end of the plunger sleeve,
   where the open slots align with the protrusion when the rotating collar is rotated to display a specific dosage in the window allowing the plunger and the plunger sleeve to slide to the dosage stop corresponding to the dosage displayed.

7. The drug delivery system of claim 6, wherein the rotating collar further comprises protrusions that are inserted into the open slots.

8. The drug delivery system of claim 1, wherein the proximal end of the plunger sleeve is affixed to the plunger flange.

9. The drug delivery system of claim 1, further comprising detents engaging the rotating collar to reversibly stop the rotation at the dosage information displays.

10. The drug delivery system of claim 9, wherein the detents comprise an insert in an indentation in the rotating collar, wherein the insert surrounding the proximal end of the outer housing and comprises gaps that align with shallow protrusions in the proximal end of the outer housing at a display of each dosage in the window of the rotating collar.

11. The drug delivery system of claim 1, wherein the dosage stop engagement mechanism comprises an inwardly directed locking finger at the distal end of the plunger sleeve engaging an outwardly directed knob at the dosage stop.

12. The drug delivery system of claim 11, wherein the dosage stop engagement mechanism further comprises an outwardly and distally directed ramp proximal to the knob, with a gap between the ramp and the knob so that the locking finger ascends the ramp and drops into the gap when the plunger sleeve moves distally along the inner housing to the dosage stop corresponding to the dosage indicated in the window, wherein engaging the mechanism at a dosage stop prevents retraction of the plunger.

13. The drug delivery system of claim 1, wherein the inner housing further comprises a distally deposed administration tip, suitable for administration of a medicament.

14. The drug delivery system of claim 1, further comprising a cap enclosing the distal portion of the outer housing.

15. The drug delivery system of claim 13, wherein the administration tip is suitable for rectal administration.

16. The drug delivery system of claim 1, wherein the syringe body comprises diazepam.

17. An adjustable dose drug delivery system comprising:
a plunger, a syringe body, an inner housing, a plunger sleeve, an outer housing, a rotating collar and a locking collar, wherein
the plunger comprises a stopper at a distal end, a plunger flange comprising a center at a proximal end, and a plunger stem fixed to the center of the plunger flange at the proximal end;
the syringe body is glass and comprises a syringe tip at a distal end and an open proximal end comprising a syringe body flange,
wherein the plunger is slidably deposed by inserting the stopper into the open proximal end of the syringe body and pushing the plunger flange toward the syringe body distal end;
the inner housing comprises a proximal end and a distal end and encloses the syringe body and is affixed thereto,
wherein the inner housing further comprises a plurality of dosage stops spirally deposed between the inner housing proximal end and distal end;
the plunger sleeve is distal to the plunger flange, and has a circumference within a plunger flange circumference and distal thereto, and encloses, and is external to, the plunger stem, and is deposed outside the inner housing and, when pushed toward the syringe body distal end, slides along the inner housing toward the plurality of dosage stops,
wherein the plunger sleeve further comprises
a closed slot running parallel to the plunger stem, and
a dosage stop engagement mechanism that engages a dosage stop when the plunger sleeve slides along the inner housing, said engagement preventing (a) further sliding of the plunger sleeve along the inner housing and (b) further insertion of the plunger toward the syringe body distal end,
wherein the dosage stop engagement mechanism comprises
an inwardly directed locking finger at the distal end of the plunger sleeve engaging an outwardly directed knob at the dosage stop,
and an outwardly and distally directed ramp proximal to the knob, with a gap between the ramp and the knob so that the locking finger ascends the ramp and drops into the gap when the plunger sleeve moves distally along the inner housing to the dosage stop corresponding to the dosage indicated in the window;
the outer housing encompasses the inner housing and comprises a proximal end overlapping and deposed outside the plunger sleeve;
the rotating collar surrounds the plunger sleeve and the proximal end of the outer housing and is rotationally joined to the plunger sleeve by a pin in the rotating collar inserted into the plunger sleeve closed slot, wherein
the rotating collar further comprises a window displaying dosage information present on the outer housing, and
rotating the rotating collar displays a series of specific dosages in the window and rotates the plunger sleeve to align the dosage stop engagement mechanism to a dosage stop on the inner housing corresponding to the specific dosage displayed in the window;
the locking collar surrounds the plunger sleeve and the proximal end of the outer housing adjacent to the rotating collar and rotationally joined thereto, wherein
the rotating collar is initially separated from the locking collar by a gap, wherein closing the gap engages a locking mechanism preventing rotation of the rotating collar and plunger sleeve,
wherein the locking mechanism comprises inwardly directed tabs on the locking collar nearest to the outer housing engaging notches in the outer housing at the position of each dosage stop;
the system further comprising an initial stop mechanism preventing, without rotating the rotating collar to display dosage information, (i) sliding of the plunger sleeve along the inner housing toward the plurality of stops and (ii) insertion of the plunger toward the syringe body distal end,
wherein the initial stop mechanism is (A) a protrusion on the inner housing above the dosage stops, and (B) open slots in the plunger sleeve extending from near the proximal end and opening at the distal end of the plunger sleeve,
where the open slots align with the protrusion when the rotating collar is rotated to display a specific dosage in the window allowing the plunger and the plunger sleeve to slide to the dosage stop corresponding to the dosage displayed.

18. A method of administering a medicament to a patient, the method comprising administering the medicament using the drug delivery system of claim 1, wherein the medicament is initially inside the syringe body and a dosage of the medicament is administered through the distal end of the syringe body or outer housing.

19. The method of claim 18, further comprising
rotating the rotating collar and plunger sleeve until a desired dosage appears in the window of the rotating collar,
applying a distal end of the system to an administration point of the patient, and
pushing the plunger and plunger sleeve until the dosage stop engagement mechanism engages the dosage stop corresponding to the desired dosage.

20. A method of administering a medicament to a patient, the method comprising administering the medicament using the drug delivery system of claim 15, wherein the medicament is initially inside the syringe body and a dosage of the medicament is administered through the distal end of the syringe body or outer housing.

* * * * *

UNITED STATES PATENT AND TRADEMARK OFFICE
CERTIFICATE OF CORRECTION

| | | |
|---|---|---|
| PATENT NO. | : 11,351,307 B2 | |
| APPLICATION NO. | : 16/346849 | |
| DATED | : June 7, 2022 | |
| INVENTOR(S) | : Lawrence J. Kelly | |

It is certified that error appears in the above-identified patent and that said Letters Patent is hereby corrected as shown below:

On the Title Page

Please replace item (71) the Applicant name of "Beloteca, Inc." with --Beloteca Investment Fund 1, LLC--.

Signed and Sealed this
Thirteenth Day of February, 2024

Katherine Kelly Vidal
*Director of the United States Patent and Trademark Office*